US008921059B2

(12) United States Patent
Murakami et al.

(10) Patent No.: US 8,921,059 B2
(45) Date of Patent: Dec. 30, 2014

(54) METHOD AND KIT FOR DETECTION OF GUAIACOL-PRODUCING BACTERIUM

(75) Inventors: Hiroaki Murakami, Kanagawa (JP); Masanori Takase, Kanagawa (JP)

(73) Assignee: Calpis Co., Ltd., Tokyo (JP)

( * ) Notice: Subject to any disclaimer, the term of this patent is extended or adjusted under 35 U.S.C. 154(b) by 386 days.

(21) Appl. No.: 13/378,274

(22) PCT Filed: Jun. 15, 2010

(86) PCT No.: PCT/JP2010/003956
§ 371 (c)(1),
(2), (4) Date: Feb. 16, 2012

(87) PCT Pub. No.: WO2010/146830
PCT Pub. Date: Dec. 23, 2010

(65) Prior Publication Data
US 2012/0135456 A1     May 31, 2012

(30) Foreign Application Priority Data

Jun. 15, 2009    (JP) ................................ 2009-142242
Sep. 28, 2009    (JP) ................................ 2009-222796

(51) Int. Cl.
*G01N 33/554*      (2006.01)
*C12Q 1/04*        (2006.01)

(52) U.S. Cl.
CPC . *C12Q 1/04* (2013.01); *C12Q 1/045* (2013.01)
USPC ....................................................... 435/7.32

(58) Field of Classification Search
USPC ....................................................... 435/7.32
See application file for complete search history.

(56) References Cited

U.S. PATENT DOCUMENTS

| 5,843,699 A | 12/1998 | Strenkoski et al. |
| 2005/0272115 A1 | 12/2005 | Niwa et al. |

FOREIGN PATENT DOCUMENTS

| EP | 0 877 092 A1 | 11/1998 |
| JP | 7-123998 A | 5/1995 |
| JP | 10-313892 A | 12/1998 |
| JP | 2003-000259 A | 1/2003 |
| JP | 2004-41104 A | 2/2004 |
| JP | 2004-141058 A | 5/2004 |
| JP | 2004-201668 A | 7/2004 |

OTHER PUBLICATIONS

Narbad et al. "Metabolism of ferulic acid via vanillin using a novel CoA-dependent pathway in a newly-isolated strain of *Pseudomonas fluorescens*", Microbiology, 1998, 144:1397-1405.*
Roling et al. "Microorganisms with a taste for vanilla: microbial ecology of traditional indonesian vanilla curing", Applied and Environmental Microbiology, 2001, 67(5):1995-2003.*
"The Unified Test Method for Thermo-Acidophilic Bacilli," Japan Fruit Juice Association, p. 25, (4 pages provided) Aug. 31, 2005.
Fujita et al., "Evaluation for Detection Meduim of Genus *Alicyclobacillus*," Kaju Kyokaiho, No. 607, pp. 1-7, 2009.
Goto et al., "Affect of oxidation and bacterial enzyme on gualacol producing pathway in orange juice," Japan Fruit Juice Association Newsletter (Kaju Kyokai Ho), No. 568, Dec. 2005, pp. 1-15.
Goto, "Thermo-Acidophilic spore-forming Bacteria: Bacteria belonging to the Genus *Alicyclobacillus*," Journal of Antibacterial and Antifungal Agents, vol. 28, No. 8, 2000, pp. 499-508 (reprinted as pp. 15-24).
International Preliminary Report on Patentability for International Application No. PCT/JP2010/003956 mailed Dec. 15, 2011.
International Search Report for International Application No. PCT/JP2010/003956 mailed Sep. 7, 2010.
Matsubara et al., "Inryo Yugaikin A.acidoterrestris no Jinsoku Kenshutsuho no Kaihatsu," Heisei 14 Nendo (Dai 45 kai) Kaju Gijutsu Kenkyu Happyokai Tokubetsu Koen Oyobi Kenkyu Happyo Yoshi, pp. 19-20, Sep. 13, 2002.
Shinsei Kagaku jikken Koza 17 Biseibutsu Jikkenho, Tokyo Kagaku Dojin, Mar. 23, 1992, 1st edition, pp. 35.
Extended European Search Report for corresponding Application No. 10789212.7 dated Nov. 26, 2012.

* cited by examiner

*Primary Examiner* — Bin Shen
(74) *Attorney, Agent, or Firm* — Birch, Stewart, Kolasch & Birch, LLP

(57) ABSTRACT

Disclosed is a method for detecting guaiacol-producing bacteria in a specimen comprising culturing the specimen or a dilution thereof on a plate of a solid medium for acidophilic bacteria comprising a compound represented by the following formula, wherein R is —H, —OH, —C(O)H, —C(O)CH$_3$, —COOH, C$_1$-C$_3$ alkyl or C$_1$-C$_3$ alkenyl, wherein alkyl and alkenyl may optionally be substituted by —OH, —C(O)H or —COOH); and detecting a colony formed on the solid medium. According to preferred embodiments, the solid medium for acidophilic bacteria comprises 50 ppm or more of vanillic acid and the plate culture is carried out at 20° C. to 55° C. The present invention also provides a solid medium for acidophilic bacteria and a kit for detection of guaiacol-producing bacteria in a specimen. According to the present invention, guaiacol-producing bacteria present in a specimen such as fruit juice raw materials can be detected rapidly in a simple manner.

11 Claims, No Drawings

METHOD AND KIT FOR DETECTION OF GUAIACOL-PRODUCING BACTERIUM

RELATED APPLICATION

The present application is a 371 national phase application of PCT/JP2010/003956 filed Jun. 15, 2010, and PCT/JP2010/003956 claims the priority from the Japanese Patent Application No. 2009-142242 filed on Jun. 15, 2009 and Japanese Patent Application No. 2009-222796 filed on Sep. 28, 2009, the contents of all the above-described applications are hereby incorporated by reference.

TECHNICAL FIELD

The present invention relates to a method and kit for detection of guaiacol-producing bacteria in fruit juice raw materials.

BACKGROUND ART

It has been known that fruit juice raw materials to be processed into fruit juice drinks and fruit juice processed food products may contain thermotolerant acidophilic bacteria (TAB) which are viable in conventional acidic drinks even under heat sterilization conditions of food products. Among typical thermotolerant acidophilic bacteria belonging to the genus *Alicyclobacillus, Alicyclobacillus acidoterrestris* (AAT) and *Alicyclobacillus acidiphilus* (AAP) have been known as the bacteria that produce guaiacol (hereinafter referred to as guaiacol-producing bacteria). Particularly, AAT bacteria have been reported to produce guaiacol via vanillin and vanillic acid (Japan Fruit Juice Association Newsletter (*KAJU KYOKAI HO*), December 2005, p. 1-15; Non-Patent Document 2). Guaiacol is not toxic, but has an unusual odor. Thus, products such as drinks containing guaiacol-producing bacteria have significantly deteriorated flavor. In many cases, AAT in fruit juice raw materials was identified to be a primary cause. Therefore, it is very important to assay the presence of guaiacol-producing bacteria in fruit juice raw materials and fruit juice drink products for quality controls of raw materials and products.

It has been known that AAT can be detected by a method comprising adding a fruit juice drink to a liquid medium containing vanillin, incubating the mixture and measuring the odor of guaiacol by a sensory test (Japanese Patent Application Laid-open No. H7-123998; Patent Document 1); or by a method for detecting the presence of guaiacol-producing bacteria comprising incubating a solution containing a specimen in the presence of vanillic acid and treating the produced guaiacol with peroxidase to develop a color followed by a qualitative or spectrometric quantitative analysis using a particular equipment (Japanese Patent Application Laid-open No. 2004-201668; Patent Document 2); or by PCR detection using primers specific to the gene of a guaiacol producing enzyme (Japanese Patent Application Laid-open No. 2003-000259; Patent Document 3).

The technique based on the above Patent Document 2 is now widely used for AAT detection with an indirect assay for the presence of AAT comprising culturing a specimen in a liquid medium containing vanillic acid and detecting the produced guaiacol with a peroxidase method.

However, the peroxidase method accompanies complicated procedures and requires a prolonged time before obtaining results because an adequate preculture step is required to grow AAT in a liquid medium. For example, in order to quantitatively detect AAT in a specimen, it is necessary to form colonies on a plate medium, pick more than one colony and culture respective colonies in a liquid medium, which are complicated procedures and require a period of 4 to 6 days.

Moreover, in the peroxidase method, the presence or absence of AAT is determined by brownish coloration produced by transformation of guaiacol to tetraguaiacol by the action of peroxidase; thus, determination may be difficult when a specimen is a raw material or medium having similar color such as orange juice. A certain skill is required for personnel who perform visual colorimetric determinations, because the color is influenced by different lots of raw materials and from conditions for autoclaving the media. For accurate determinations, spectrophotometric analysis with calibration curves for each specimen and medium, or GC-MS analysis are required, and thus expensive analyzers and complex procedures are further required.

Another known method using a solid medium is a 30° C.-culture method, where guaiacol-producing bacteria are distinguished from guaiacol non-producing bacteria based on culture temperatures. For example, a specimen is cultured at 30° C., which is lower than an optimal growth temperature of AAT (40 to 50° C.), and the presence or absence of colonies is determined. Because the growth of AAT is also decreased in culture at 30° C., the sensitivity of detection of AAT is low and guaiacol non-producing bacteria of no interest having a lower optimal growth temperature range will also emerge. Accordingly, a preculture step is required for the 30° C.-culture method in order to improve the sensitivity of detection of AAT. In this case, all the steps may take as long time as 8 to 10 days, and the selectivity is not sufficient. Moreover the method is not quantitative because the preculture step is required.

In addition, it has been known that components such as polyphenols contained in citrus fruits and grapes may inhibit the growth of AAT. Thus, a specimen needs to be appropriately diluted before an assay of raw materials having high fruit concentrations such as 100% fruit juices. For example, orange juice is diluted to 1% before an assay. However, the dilution factor needs to be reviewed per type of fruit juice and the production area thereof, making the above assay procedures more complicated.

Therefore, there still exist a need for a quick and accurate method for determination of the presence or absence of guaiacol-producing bacteria in fruit juice raw materials without requiring complicated procedures, expensive equipments or a skill of operators. There is also a need for a convenient method which allows assays at the sites of production of fruits and in facilities for production of fruit juice raw material.

The references cited in the present application are as follows. The contents thereof are entirely incorporated herein by reference.

Patent Document 1: Japanese Patent Application Laid-open No. H7-123998

Patent Document 2: Japanese Patent Application Laid-open No. 2004-201668

Patent Document 3: Japanese Patent Application Laid-open No. 2003-000259

Non-Patent Document 1: "The Unified Test Method for Thermo-Acidophilic Bacilli", Japan Fruit Juice Association, 2005, p. 25

Non-Patent Document 2: Japan Fruit Juice Association Newsletter (*KAJU KYOKAI HO*), December 2005, p. 1-15

DISCLOSURE OF THE INVENTION

An object of the present invention is to provide a rapid and simple method for detection of guaiacol-producing bacteria in a specimen such as fruit juice raw materials.

The present inventors have found that guaiacol-producing bacteria can selectively grow and form a colony on a solid medium comprising a compound having a methoxyphenol skeleton at a specific concentration range. The detection of formation of a colony on the solid medium allows convenient detection of the presence or absence of guaiacol-producing bacteria in a test sample, and counting of the number of a colony allows convenient measurement of the number of guaiacol-producing bacteria in the test sample.

The present invention provides a method for detecting guaiacol-producing bacteria in a specimen, comprising culturing the specimen or a dilution on a solid medium for acidophilic bacteria comprising one or more of a compound represented by the following formula:

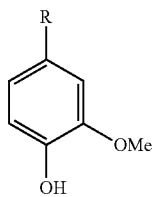

wherein R is —H, —OH, —C(O)H, —C(O)CH$_3$, —COOH, C$_1$-C$_3$ alkyl or C$_1$-C$_3$ alkenyl, wherein alkyl and alkenyl may optionally be substituted by —OH, —C(O)H or —COOH); and detecting a colony formed on the solid medium. More specifically, the present invention provides a method which allows direct detection and quantification of guaiacol-producing bacteria without requiring a preculture step or a treatment step for qualitative analysis (color development by the peroxidase method) that is required in the conventional methods. The compound is preferably selected from the group consisting of vanillin, vanillic acid, ferulic acid, guaiacol, 4-hydroxy-3-methoxyphenylacrylaldehyde, 4-hydroxy-3-methoxyphenyl propionic acid, 4-hydroxy-3-methoxyphenylmethyl alcohol, methoxyhydroquinone, 4-hydroxy-3-methoxyphenyl acetaldehyde and 4-vinylguaiacol. The compound is more preferably vanillin, vanillic acid or ferulic acid.

Particularly preferably, the solid medium for acidophilic bacteria contains 50 ppm or more of vanillic acid; 500 ppm or more of vanillin, or 25 ppm or more of ferulic acid. More preferably, the solid medium for acidophilic bacteria contains from 50 ppm to 225 ppm, still more preferably from 50 ppm to 75 ppm of vanillic acid. Preferably, the plate culture is carried out at 20° C. to 55° C., more preferably at 30° C. to 45° C., particularly preferably at 30° C. (27° C. to 33° C.). In the present invention, it can be expected that a temperature within ±10% difference may provide a similar effect.

In another aspect, the present invention provides a kit for detecting guaiacol-producing bacteria in a specimen comprising a sterilized solid medium for acidophilic bacteria comprising a compound having a methoxyphenol skeleton, particularly vanillin, vanillic acid or ferulic acid.

In another aspect, the present invention provides a selection medium for guaiacol-producing bacteria comprising a solid medium for acidophilic bacteria comprising a compound having a methoxyphenol skeleton, particularly any of vanillin, vanillic acid and ferulic acid.

According to the present invention, guaiacol-producing bacteria in specimens such as fruit juice raw materials can be detected rapidly in a simple manner.

PREFERRED EMBODIMENTS OF THE INVENTION

The method for detecting guaiacol-producing bacteria according to the present invention comprises culturing a specimen or a dilution thereof on a plate of a solid medium for acidophilic bacteria comprising a compound having a methoxyphenol skeleton, preferably vanillin, vanillic acid or ferulic acid, and detecting a colony formed on the plate. Guaiacol-producing bacteria produce guaiacol via vanillin and vanillic acid. It is reported that ferulic acid is a vanillin related substance, but is not directly involved in production of guaiacol by AAT. The present invention is based on the finding that vanillic acid does not inhibit growth of guaiacol-producing bacteria, while it inhibits the growth of bacteria of the genus *Alicyclobacillus* which do not produce guaiacol. Although AAT was known to produce guaiacol in a medium containing vanillic acid, it was found for the first time in the present invention that the growth rate of guaiacol-producing bacteria is different from that of guaiacol non-producing bacteria on a solid medium containing vanillic acid. According to the present invention, the growth of guaiacol non-producing bacteria is suppressed to allow a preferential growth of guaiacol-producing bacteria, so that the guaiacol-producing bacteria can be selectively detected.

The specimen to be assayed by the method of the present invention includes raw materials, semi-processed materials and products for drinks and foods, which are suspected to contain thermotolerant acidophilic bacteria. More specifically, it includes acidic fruit juice raw materials such as orange juice, apple juice and mandarin orange juice, semi-processed materials thereof, concentrated juice thereof and drinks and foods produced from these fruit juice raw materials. Thermotolerant acidophilic bacteria are not completely killed under the heat treatment conditions conventionally used for sterilization of drinks and foods, and they may grow in products containing diluted fruit juice, although they may not grow in concentrated fruit juices due to the presence of inhibitors. Therefore, any samples may be assayed by the method of the present invention for quality controls depending on the properties of raw materials and products as well as on distribution systems. According to the method of the present invention, guaiacol-producing bacteria can be directly detected and directly quantitated by counting the number of colonies formed on the medium, and a preculture step or a treatment step for verification (color development by the peroxidase method) required in the conventional methods is not necessary.

The medium for guaiacol-producing bacteria according to the present invention and the kit for detection of guaiacol-producing bacteria utilizing the medium do not require the use of instruments or reagents for a preculture step and a treatment step for verification, and will contribute to rapid and simple assay with a compact kit.

The guaiacol-producing bacteria to be detected by the method of the present invention are primarily *Alicyclobacillus acidoterrestris* (AAT) and *Alicyclobacillus acidiphilus* (AAP), which have been already identified. Among them, AAT is frequently detected in fruit juice raw materials, while AAP is rarely detected. Thus, in view of quality controls, it may be sufficient if AAT can be detected. As described below, however, the method of the invention can be carried out under the condition that allows detection of AAT only, or under the condition that allows detection of both AAT and AAP by changing the content of vanillic acid in the medium. The method of the present invention may also be used for detection of other bacteria belonging to the genus *Alicyclobacillus* which may produce guaiacol. Such bacteria have been described in some reports but not studied in detail. Bacteria of the genus *Alicyclobacillus* which do not produce guaiacol are also known, including *Alicyclobacillus acidocaldarius, Alicyclobacillus pomorum* and the like.

The method of the present invention utilizes a selection medium where only guaiacol-producing bacteria selectively form colonies. The selection medium is a solid medium for acidophilic bacteria comprising one or more of a compound having a methoxyphenol skeleton represented by the formula:

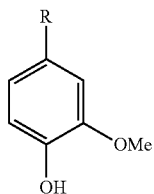

wherein R is —H, —OH, —C(O)H, —C(O)CH$_3$, —COOH, C$_1$-C$_3$ alkyl or C$_1$-C$_3$ alkenyl, wherein alkyl and alkenyl may optionally be substituted by —OH, —C(O)H or —COOH.

The compound having a methoxyphenol skeleton preferably includes vanillin (R=C(O)H), vanillic acid (R=COOH), ferulic acid (R=CH=CH—COOH), guaiacol (R=H), 4-hydroxy-3-methoxyphenylacrylaldehyde (R=CH=CH—C(O)H), 4-hydroxy-3-methoxyphenyl propionic acid (R=CH$_2$CH$_2$COOH), 4-hydroxy-3-methoxyphenylmethyl alcohol (R=CH$_2$OH), methoxyhydroquinone (R=OH), 4-hydroxy-3-methoxyphenyl acetaldehyde (R=C(O)CH$_3$) and 4-vinylguaiacol (R=CH$_2$=CH$_2$). All of these compounds have been reported to be produced by microorganisms as metabolites of ferulic acid.

Particularly preferably, the compound having a methoxyphenol skeleton is selected from vanillin, vanillic acid and ferulic acid. Alternatively, a mixture of two or three of vanillin, vanillic acid and ferulic acid may also be used. Any of media generally used for acidophilic bacteria may be used in the present invention. A preferred medium is YSG medium (containing yeast extract, soluble starch and glucose, pH3.0 to 4.0) which is easily available and has been studied extensively. Vanillin, vanillic acid and ferulic acid are commercially available. The concentration of vanillin, vanillic acid or ferulic acid to be added to the medium can be selected as follows depending on whether detection of both AAT and AAP is required, or detection of only AAT is sufficient.

When detection of only AAT is sufficient, 50 ppm or more of vanillic acid may be used. The concentration of vanillic acid is preferably 50 to 225 ppm, more preferably 75 to 200 ppm, still more preferably 100 to 200 ppm. When vanillin is used, the concentration may be 500 ppm or more, preferably 900 to 1000 ppm. When ferulic acid is used, the concentration may be 25 ppm to 50 ppm, preferably about 50 ppm.

When detection of both AAT and AAP is required, 50 ppm to 75 ppm of vanillic acid may be used. The conventional detection methods are mainly focused on AAT which is frequently found in a sample compared to other guaiacol-producing bacteria. In contrast, the present invention allows detection of other guaiacol-producing bacteria such as AAP by appropriately selecting the amount of vanillic acid.

Concentrations of the compounds having a methoxyphenol skeleton other than vanillin, vanillic acid and ferulic acid can also be optimized in a manner similar to the one described in the following examples.

The solid medium can be prepared according to the usual manner by adding to YSG medium agar and a predetermined amount of one or more of the compound having a methoxyphenol skeleton, sterilizing the same and allowing agar to solidify. Due to the low pH of the medium, the medium may not be sufficiently solidified when it is autoclaved with agar. Thus, it is preferable to appropriately adjust the amount of agar, or to sterilize the medium and agar separately before mixing them together, or to add an acid to adjust pH after sterilizing a mixture of a medium having near-neutral pH and agar. The solid medium may be prepared in a plate for smear application or in a flask or bottle for pour application.

According to the method of the present invention, a specimen as such or with appropriate dilution is added to the solid medium and cultured on the plate. A specimen may be serially diluted (1, 1/10, 1/100 etc.) in order to facilitate colony counting. Because the bacteria of the genus *Alicyclobacillus* form spores, it is preferable to subject a specimen to a heat-shock treatment with a heat treatment at 70° C. for 20 minutes prior to addition to the medium in order to activate the bacterial cells. When detection is carried out by a pour method, a specimen is added to and mixed with the melted agar medium and the mixture is transferred to a plate for solidification. When detection is carried out by a smear method, a specimen may be smeared on the solid medium in a plate. When detection is carried out using a membrane filter, a specimen is filtered through a membrane filter and the filter is placed on the solid medium in a plate.

The culture may be carried out at any temperature within the growth temperature range of guaiacol-producing bacteria (20° C. to 55° C.). However, in order to improve selectivity from guaiacol non-producing bacteria, it is carried out at 50° C. or lower, more preferably at 45° C. or lower, still more preferably at 40° C. or lower, particularly preferably at 30° C. (27° C. to 33° C.). In the present invention, a temperature within ±10% difference will provide a similar effect. According to the present invention, it has been surprisingly found that the detection sensitivity of guaiacol-producing bacteria is significantly improved by adding vanillic acid in a solid medium. For example, it was observed that the same number of colonies is obtained when AAT is cultured at 30° C. for 5 days and at 45° C. for 3 days on the same solid medium containing 75 ppm of vanillic acid. This means that the present invention allows an accurate quantification within the temperature range lower than the optimal growing temperature of AAT. Thus, the method of the present invention significantly improves the detection sensitivity, and is a revolutionary method which allows not only elimination of a preculture step but also more accurate, rapid and convenient quantification. Moreover, bacteria of no interest are not detected due to low temperature and the presence of vanillic acid. The same tendency was observed when vanillin or ferulic acid was used instead of vanillic acid.

The presence of absence of guaiacol-producing bacteria in a specimen can be determined by visual inspection of colonies after cultivation for a predetermined period, for example 3 to 5 days. The number of bacterial cells in a specimen can be easily calculated from the colony count and the dilution rate of the specimen. According to the present invention, accurate quantitative data can be obtained conveniently without requiring special equipments or a skill.

In another aspect, the present invention provides a kit for detection of guaiacol-producing bacteria in a specimen. The kit comprises at least a solid medium for acidophilic bacteria comprising one or more of the compound having a methoxyphenol skeleton represented by the following formula:

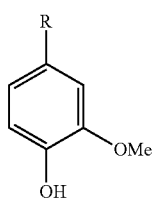

wherein R is —H, —OH, —C(O)H, —C(O)CH$_3$, —COOH, C$_1$-C$_3$ alkyl or C$_1$-C$_3$ alkenyl, wherein alkyl and alkenyl may optionally be substituted by —OH, —C(O)H or —COOH. The solid medium for acidophilic bacteria can be provided in a sterilized form in a plate, or in a flask or bottle for pour. The kit for a method involving a membrane filter may further comprise a membrane filter and a filtering device. The kit may further comprise a plate for preparation of serial dilutions, a positive control guaiacol-producing bacterium and an instruction.

The contents of all patents and references explicitly cited herein are entirely incorporated herein by reference.

The present invention is now described in further detail by way of examples, which do not limit the present invention.

Example 1

A YSG agar medium containing vanillin, vanillic acid or ferulic acid was used to study the colony formation of thermotolerant acidophilic bacteria (TAB). Four bacterial strains used were *A. acidoterrestris* ATCC49025, *A. acidiphilus* JCM21417, *A. acidocaldarius* ATCC27009 and *A. pomorum* JCM21459. Among these, *A. acidoterrestris* ATCC49025 and *A. acidiphilus* JCM21417 have been reported as the bacterial strains producing guaiacol.

A YSG medium (Merck K.K., YGS Agar; 20.0 g) and vanillic acid (Wako Pure Chemical Industries, Ltd.; 0 to 250 mg) were dissolved in 1000 g of water with heating and subjected to autoclave sterilization (121° C. and 15 min.). After cooling to about 50° C., pH was adjusted to 3.7 with 10% sulfuric acid and a plate medium was prepared.

The suspensions of the respective bacterial strains were subjected to a heat-shock treatment at 70° C. for 20 min. The bacterial suspensions were serially diluted with phosphate buffered saline up to $10^3$ CFU/mL and 100 μL from the dilutions was smeared on the plates for culture. Cultivation was carried out at 45° C. for 3 days before the colonies formed were visually inspected.

When 75 ppm of vanillic acid was added, the same level or more colonies were detected as in the medium without vanillic acid for two strains of guaiacol-producing bacteria, while no colony was detected for other two strains. When 100 ppm of vanillic acid was used, the same level or more colonies were detected as in the medium without vanillic acid for *A. acidoterrestris* ATCC49025, while no colony was detected for other three bacterial strains. At the levels of 150 ppm and 200 ppm of vanillic acid, *A. acidoterrestris* ATCC49025 was detected at the same level as in the medium without vanillic acid. The detection sensitivity of AAT was lower with 225 ppm of vanillic acid, and no colonies were detected at 250 ppm or more.

Similar experiments were carried out with replacing vanillic acid with vanillin or ferulic acid. When the medium was not easily solidified, the amount of agar was appropriately adjusted. The results of Example 1 are summarized in the tables below.

TABLE 1

Results of experiments with addition of vanillic acid
(cultivation at 45° C. for 3 days)

| Name of strain | No. | Vanillic acid concentration (ppm)* | | | | | | | |
|---|---|---|---|---|---|---|---|---|---|
| | | 10 | 50 | 75 | 100 | 150 | 200 | 225 | 250 |
| *A. acidoterrestris* | ATCC49025 | ++ | ++ | ++ | ++ | ++ | ++ | + | − |
| *A. acidiphilus* | JCM21417 | ++ | ++ | ++ | − | − | − | − | − |
| *A. acidocaldarius* | ATCC27009 | ++ | − | − | − | − | − | − | − |
| *A. pomorum* | JCM21459 | ++ | − | − | − | − | − | − | − |

Results of experiments with addition of vanillin
(cultivation at 45° C. for 3 days)

| Name of strain | | Vanillin concentration (ppm)* | | | | |
|---|---|---|---|---|---|---|
| | | 500 | 750 | 900 | 950 | 1000 |
| *A. acidoterrestris* | ATCC49025 | ++ | ++ | ++ | ++ | + |
| *A. acidiphilus* | JCM21417 | + | + | + | − | − |
| *A. acidocaldarius* | ATCC27009 | − | − | − | − | − |
| *A. pomorum* | JCM21459 | − | − | − | − | − |

Results of experiments with addition of ferulic acid
(cultivation at 45° C. for 3 days)

| Name of strain | | Ferulic acid concentration (ppm)* | | |
|---|---|---|---|---|
| | | 25 | 50 | 75 |
| *A. acidoterrestris* | ATCC49025 | ++ | ++ | − |
| *A. acidiphilus* | JCM21417 | ++ | − | − |
| *A. acidocaldarius* | ATCC27009 | − | − | − |
| *A. pomorum* | JCM21459 | − | − | − |

*"++" means the detected level was at or above the level of the medium without a substrate (i.e. YSG medium), "+" means the detected level was lower than the level of the medium without a substrate and "−" means undetectable.

Example 2

Effects of culture temperature on the detection level of colonies of *A. acidoterrestris* ATCC49025 were studied using YSG agar medium containing vanillin, vanillic acid or ferulic acid. The solid media were prepared in a similar manner as Example 1 by adding 75 ppm of vanillic acid to YSG media. The suspensions containing the same number of bacterial cells of *A. acidoterrestris* ATCC49025 were smeared on the plates and cultured at 45° C. or 30° C. A YSG medium without any substrate was used as a control.

The numbers of colonies after cultivation at 45° C. for 3 days and at 30° C. for 5 days are shown in the following table. The values are expressed as relative values to the number of colonies obtained after cultivation at 45° C. for 3 days in a YSG medium without any substrate being regarded as 100.

TABLE 2

|  | 45° C., 3 days | 30° C., 5 days |
|---|---|---|
| none | 100 | 21 |
| vanillic acid 75 ppm | 183 | 186 |

When a YSG medium without any substrate was used, cultivation at 30° C. for 5 days could produce less detectable colonies than cultivation at 45° C. for 3 days, indicating that a preculture step is required in the 30° C.-culture method.

On the other hand, when 75 ppm of vanillic acid was added, more colonies were detected at 45° C. compared to the medium without any substrate. This suggests that an addition of vanillic acid facilitated the colony formation of *A. acidoterrestris* ATCC49025, and improved the detection sensitivity. The detection sensitivity was also improved when 50 ppm of vanillic acid, 750 ppm of vanillin or 25 ppm of ferulic acid was used instead of 75 ppm of vanillic acid.

When 75 ppm of vanillic acid was added, almost the same number of colonies was detected in cultivations at 30° C. for 5 days and at 45° C. for 3 days. Combining with the result from example 1. It is demonstrated that the presence of vanillic acid suppresses the growth of guaiacol non-producing bacteria. This result shows that guaiacol-producing bacteria can be detected with high sensitivity and specificity when a specimen is cultured in the medium containing vanillic acid at 30° C.

INDUSTRIAL APPLICABILITY

The present invention is useful in quality controls of drink and food products and their production raw materials. The present invention allows direct detection as well as direct quantification of guaiacol-producing bacteria without requiring a preculture step or a treatment step for verification (color development by the peroxidase method), so that it can significantly reduce the time and cost for detection of bacteria which may deteriorate the product qualities. The kit for detection of guaiacol-producing bacteria according to the present invention is of significant industrial utility because it is compact in size and convenient, requires no instruments or reagents for a preculture step and a treatment step for verification and allows a rapid detection.

The invention claimed is:

1. A method for detecting guaiacol-producing bacteria in a specimen comprising:
    culturing the specimen or a dilution thereof on a solid medium for acidophilic bacteria, said medium comprising from 50 ppm to 225 ppm of vanillic acid, from 500 ppm to 1000 ppm of vanillin, or from 25 ppm to 50 ppm of ferulic acid; and
    detecting a colony formed on the solid medium.

2. The method according to claim 1, wherein the solid medium for acidophilic bacteria comprises from 50 ppm to 225 ppm of vanillic acid.

3. The method according to claim 1, wherein the solid medium for acidophilic bacteria comprises from 50 ppm to 75 ppm of vanillic acid.

4. The method according to claim 1, wherein the culturing step is carried out at 20° C. to 55° C.

5. The method according to claim 4, wherein the culturing step is carried out at 27° C. to 33° C.

6. The method according to claim 1, wherein the guaiacol-producing bacteria is thermotolerant acidophilic bacteria (TAB).

7. The method according to claim 1, wherein the guaiacol-producing bacteria is bacteria belonging to the genus *Alicyclobacillus*.

8. The method according to claim 1, wherein the guaiacol-producing bacteria is *Alicyclobacillus acidoterrestris* and/or *Alicyclobacillus acidiphilus*.

9. The method according to claim 1, wherein the specimen includes fruit juice.

10. The method according to claim 1, wherein the medium has a pH of from 3.0 to 4.0.

11. The method according to claim 1, wherein the solid medium for acidophilic bacteria comprises from 50 ppm to 75 ppm of vanillic acid or 500 ppm to 900 ppm of vanillin.

* * * * *